(12) United States Patent
Oberlin

(10) Patent No.: US 7,691,254 B2
(45) Date of Patent: Apr. 6, 2010

(54) METHOD OF CHECKING THE FUNCTION OF A SENSOR

(75) Inventor: Rene Oberlin, Wuerenlos (CH)

(73) Assignee: Mettler-Toledo AG, Greifensee (CH)

( * ) Notice: Subject to any disclaimer, the term of this patent is extended or adjusted under 35 U.S.C. 154(b) by 1052 days.

(21) Appl. No.: 11/276,988

(22) Filed: Mar. 20, 2006

(65) Prior Publication Data

US 2006/0219575 A1    Oct. 5, 2006

(30) Foreign Application Priority Data

Apr. 1, 2005    (EP)    ................... 05102599

(51) Int. Cl.
*G01N 27/26*    (2006.01)
(52) U.S. Cl. .................... 205/775; 204/401
(58) Field of Classification Search ......... 204/400–435; 205/775, 794.5
See application file for complete search history.

(56) References Cited

U.S. PATENT DOCUMENTS

| | | | | |
|---|---|---|---|---|
| 5,174,884 A | * | 12/1992 | Shimada et al. | 204/406 |
| 5,202,637 A | * | 4/1993 | Jones | 324/425 |
| 5,470,484 A | * | 11/1995 | McNeel | 210/746 |
| 5,650,061 A | * | 7/1997 | Kuhr et al. | 205/775 |
| 5,980,708 A | * | 11/1999 | Champagne et al. | 204/406 |
| 6,428,684 B1 | | 8/2002 | Warburton | |
| 6,761,817 B2 | | 7/2004 | Connery | |
| 2001/0045119 A1 | * | 11/2001 | Warburton | 73/23.21 |
| 2005/0247572 A1 | * | 11/2005 | Scheffler | 205/775 |

FOREIGN PATENT DOCUMENTS

| | | |
|---|---|---|
| CH | 636 447 A5 | 5/1983 |
| DE | 102 44 084 A1 | 4/2004 |
| EP | 0 039 549 A2 | 11/1981 |

* cited by examiner

*Primary Examiner*—Nam X Nguyen
*Assistant Examiner*—Jennifer Dieterle
(74) *Attorney, Agent, or Firm*—Standley Law Group LLP

(57) ABSTRACT

The functioning of an amperometric electrochemical sensor having an electrochemical cell is monitored by the electrochemical cell. A perturbation quantity is imposed on the sensor, which is operated with voltage control at a given polarization voltage. The response to the perturbation is measured and a check value is calculated, using the response under the perturbation as an input value. The check value is compared to a system-dependent limit value. If the check value is larger than the system-dependent limit value, the initial polarization voltage is changed by a predefined voltage increment and the process is repeated, until an optimal polarization voltage has been found, i.e., until the calculated check value is smaller than the system-dependent limit value. A measuring system that serves to carry out the method is also described. An automated embodiment utilizes a computer-supported control- and processing-unit with a data memory and a data-evaluating program.

18 Claims, 5 Drawing Sheets

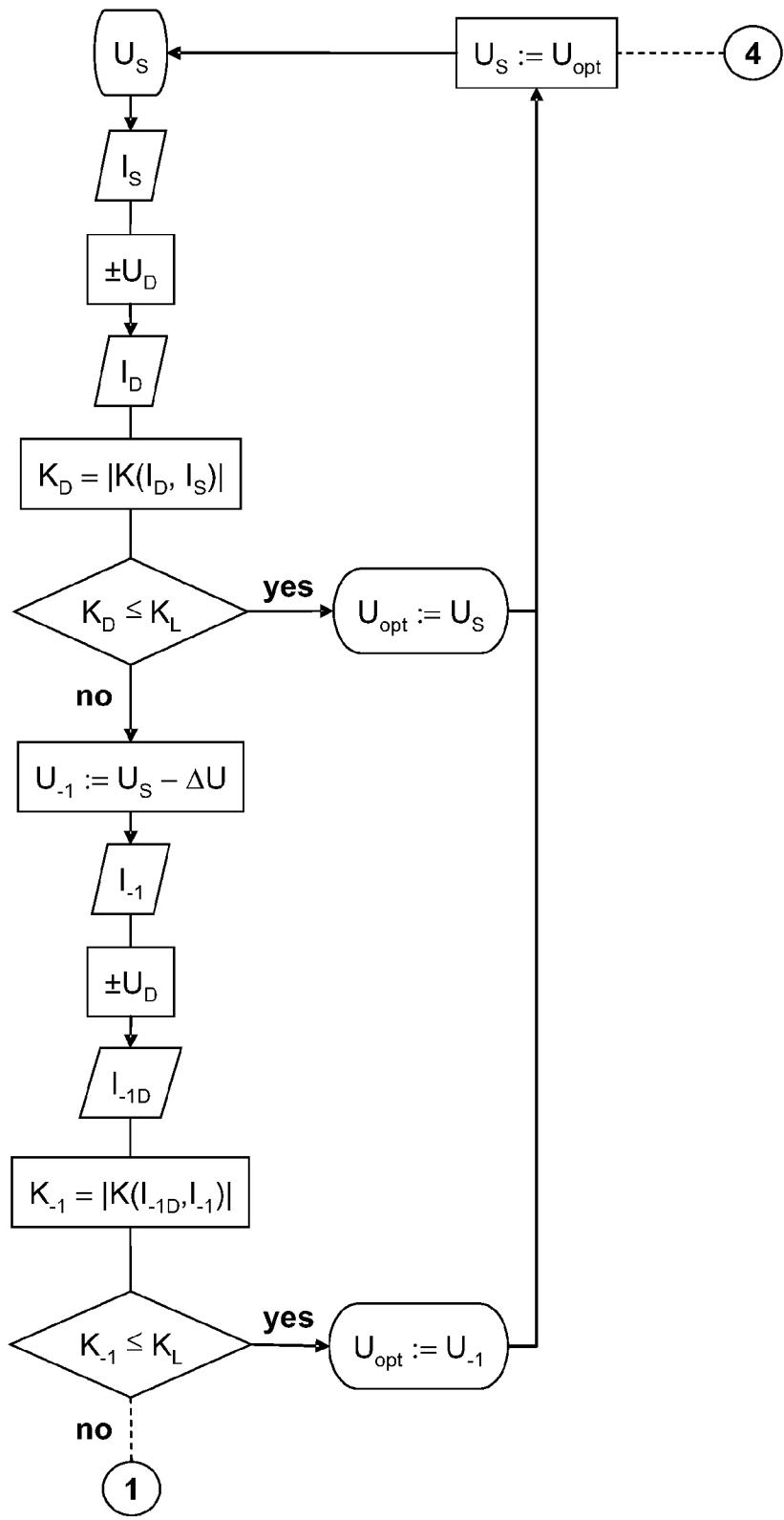
Fig. 1 (Part 1)

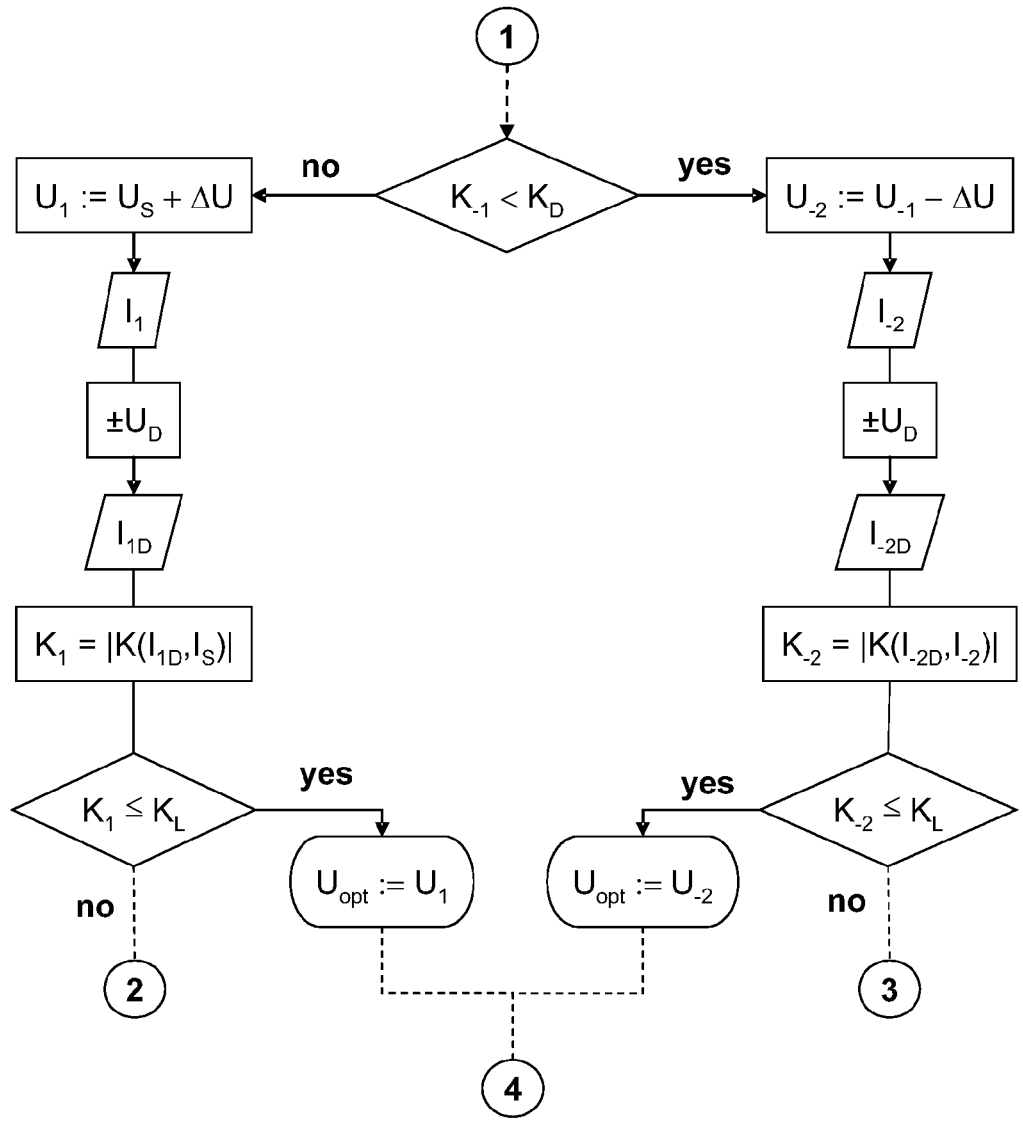
Fig. 1 (Part 2)

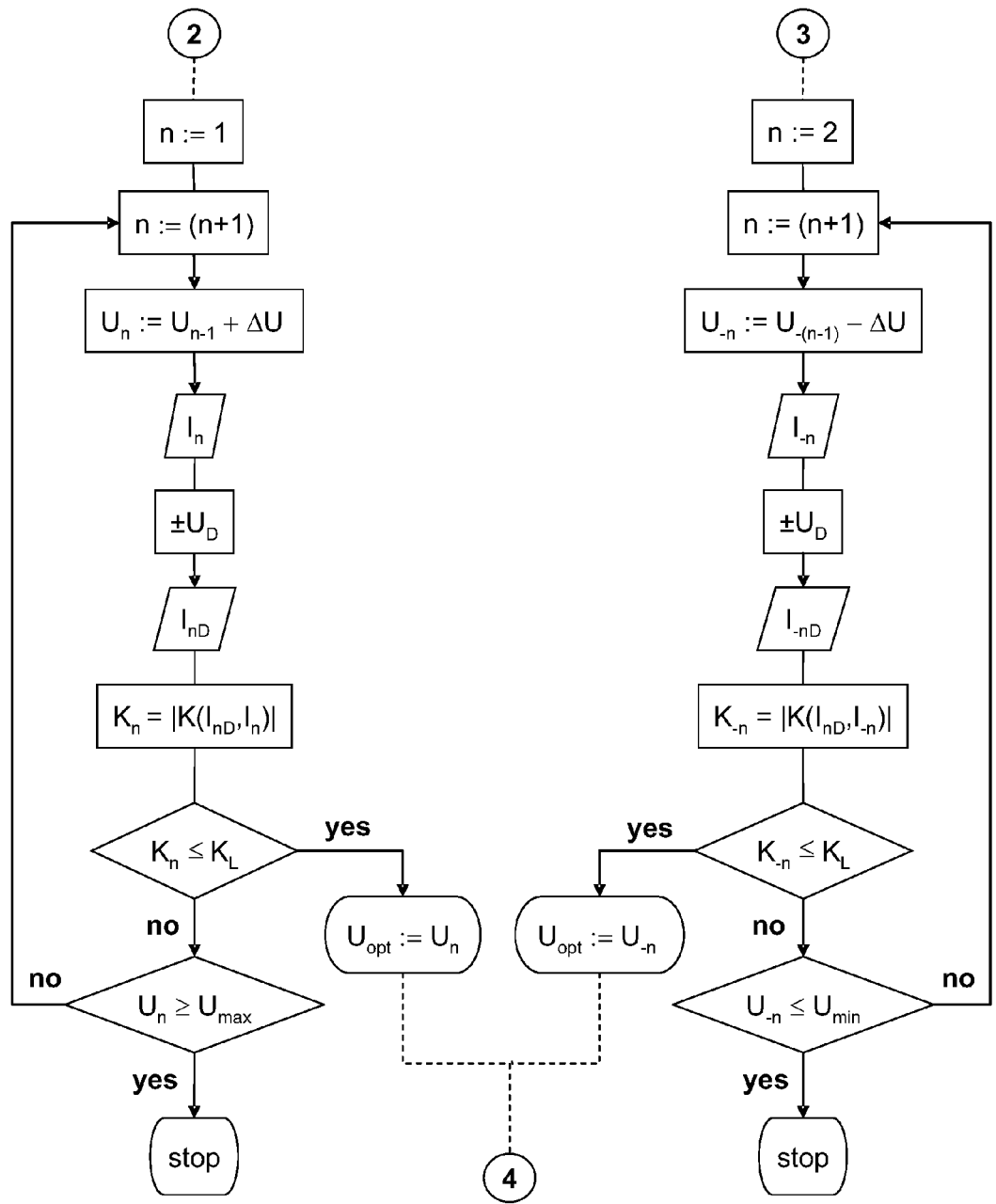
Fig. 1 (Part 3)

METHOD OF CHECKING THE FUNCTION OF A SENSOR

TECHNICAL FIELD

The invention relates to a method of checking whether an amperometric electrochemical sensor is functioning correctly.

BACKGROUND OF THE ART

Amperometric electrochemical sensors are used in a variety of areas for the determination of the partial pressure and/or the concentration of gases dissolved in fluids. The gases can be dissolved in liquids as well as in gases. The known state of the art includes sensors for the determination of ozone, chlorine, hydrogen and oxygen, among others. These sensors are used in different areas such as the chemical industry, the food industry, and in the field of biotechnology, for example to monitor processes or also for waste water analysis.

The measuring principle of amperometric electrochemical sensors is based on measuring the electrical current that flows between at least two electrodes in an electrochemical cell when a specific bias voltage or polarization voltage is applied. The sensor in many cases also includes a thin, gas-permeable membrane which separates the test medium from the electrochemical cell and allows only certain volatile or gaseous substances, e.g. oxygen, to pass through. However, there are also sensors without a membrane of this kind.

The electrochemical cell has at least two electrodes and an electrolyte solution in which the electrodes are immersed. At least one of the electrodes is a working electrode and at least one is a counter-electrode. In addition, there may also be a reference electrode. The counter-electrode as well as the reference electrode are immersed in an ion-conducting electrolyte solution that is also in contact with the working electrode. Through appropriate means, the working electrode is operated at a specific voltage which is often negative in relation to the counter-electrode. In other words, the working electrode is often configured as cathode.

In an amperometric electrochemical sensor with an oxygen-permeable membrane, i.e., in an oxygen sensor, oxygen dissolved in the medium migrates through the membrane to the cathode. At the cathode, oxygen is electrochemically reduced to water in accordance with the following chemical equation:

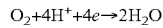

The counter-electrode, in most cases configured as anode, is often constituted by a silver/silver-chloride electrode. At a counter-electrode of this type, silver is oxidized into silver chloride as described by the following chemical equation:

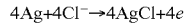

If a constant voltage is applied to the electrochemical cell, the chemical reactions at the electrodes will cause a measurable electrical current to flow between the anode and the cathode. The measured current is in direct proportion to the partial pressure and, accordingly, to the concentration of the substance that is dissolved in the medium if the oxygen that is present at the cathode is consumed completely so that the partial pressure of oxygen at the cathode equals zero. With the exception of the partial pressure, almost all of the characteristic parameters of a sensor are dependent on the temperature, so that one needs to state all measurement values and characteristic parameters as functions of temperature or to put them into relation to a standard temperature. The measurements are therefore generally made with temperature compensation, with the actual temperature being determined by means of at least one temperature sensor.

The driving force for the electrode reaction is supplied by the oxygen diffusion through the gas-permeable membrane, in which the partial-pressure differential at the membrane is the determining factor. If all of the oxygen present at the cathode is reduced, the oxygen flow is controlled exclusively by the difference in the partial pressures at the membrane.

Amperometric electrochemical oxygen sensors are generally operated with voltage control, with the applied voltage being referred to as polarization voltage. In a typical voltammogram, i.e., a diagram of current vs. voltage, for the reduction of dissolved oxygen the current as a function of a decreasing negative voltage rises at first up to a plateau where the current remains substantially constant over a certain voltage range, beyond which the current increases further with a continuing decrease in voltage.

The plateau in the voltammogram is characteristic of a voltage range in which the oxygen reduction is controlled by the rate of diffusion and the partial pressure at the cathode equals zero.

In general, the polarization voltage of the sensor is selected so that the partial pressure of oxygen inside the sensor, more specifically at the cathode, equals zero and all of the oxygen that is present at the cathode is being reduced. This optimum level for the polarization voltage should be located approximately in the middle of the plateau in a typical voltammogram. The measured current is in this case voltage-independent and directly proportional to the partial pressure and the concentration of the oxygen dissolved in the medium.

If the polarization voltage deviates from the optimal polarization voltage, i.e., if the polarization voltage no longer lies in the middle of the plateau or if it lies even outside of the plateau, one of the two electrode reactions will occur with preference over the other. A polarization voltage that is too low has the effect that less oxygen is reduced to water, while a polarization voltage that is too high will have the effect that even water is reduced to hydrogen. Thus, a polarization voltage that deviates from the optimal polarization voltage leads to errors in the measurement results for the current.

The optimal polarization voltage and with it the shape and location of the plateau in the voltammogram depend on a variety of factors. The ability of the sensor to function correctly is influenced by these factors which include, among others, the temperature, the geometry of the sensor, the age of the sensor, as well as a variety of properties of the electrolyte solution in the sensor and of the test medium, such as for example the pH value, the oxygen concentration, as well as the presence of interfering substances such as carbon dioxide or other volatile components that can pass through the membrane and enter into a chemical reaction at the electrodes.

The different fields of application of amperometric electrochemical sensors impose strong requirements on the ability of a sensor to function correctly. A variety of methods are known for checking the function of amperometric electrochemical sensors.

A method of checking the function of an electrochemical sensor, in particular a conductivity sensor or pH sensor, is disclosed in German published application 102 44 084 A1 (8 Apr. 2004). A perturbation quantity is applied temporarily to the sensor, and the dynamic change of the sensor signal is captured during application and/or removal of the perturbation. This change in the sensor signal as a function of time is used as a measure for the changes of different characteristic sensor parameters. The perturbation quantity used in this case is constituted by an external auxiliary voltage. In the case of a pH sensor, the measuring electrode and the reference electrode are simply short-circuited with each other.

In an amperometric electrochemical oxygen sensor, the foregoing method has the disadvantage that a perturbation quantity such as, e.g., a voltage variance has to be relatively large in order to allow a dynamic dependency of the sensor signal to be observed. The voltage variance has to be sufficiently large to take the chemical system out of its equilibrium, and it should therefore lie outside of the plateau in the voltammogram. The time that elapses until the chemical equilibrium is restored, i.e., until the partial pressure at the cathode returns to zero, is relatively long and could influence the acquisition of measurement values which during a chemical process often occurs at very short time intervals. Short-term changes of the measuring system or of the medium cannot be captured during the function check of the sensor.

A method of determining the polarization voltage of an oxygen sensor is disclosed in U.S. Pat. No. 6,761,817 B2 to Connery (13 Jul. 2004). A measuring system which includes a sensor that is normally operated under voltage control is modified in such a way that the sensor can be operated with voltage control as well as current control. In order to check the polarization voltage, the sensor is switched to a current-controlled mode and the voltage responses are measured for a level of current that is raised and for another level of current that is lowered in comparison to the initial value. The voltage response in this case is represented by the voltage value measured at a specific preset level of current. The deviations from the initial current are in this case fixed, given values, and the voltage responses are determined at these two constant current levels. The optimal polarization voltage corresponds in this case approximately to the mean value of the two voltages, the specifically stated value being 56%.

This 56%-principle which is used to find the optimal polarization voltage has to be determined empirically and depends on the sensor geometry as well as on the oxygen concentration in the medium. This means that the optimal polarization voltage can only be determined if the medium and/or the measuring system are not changing during the determination process.

The given levels of current are selected so that they lie in the areas that form the limits of oxygen electrochemistry. In the practice of this method, the sensor is operated at levels of current that lie outside the plateau of a typical voltammogram, although this has the consequence that the chemical equilibrium can be disturbed for example by hydrogen being produced in the reduction of water, which causes a delay in reaching the chemical equilibrium following the process of determining the polarization voltage. After the polarization voltage has been determined, the sensor is switched back to the voltage-controlled mode, and the new semi-empirically determined polarization voltage is set. Depending on how strongly the sensor has been disturbed, an extended waiting period has to be observed until stable measurement values can be determined.

However, especially in sensitive areas such as the food industry and/or the field of biotechnology it is extremely important that changes in the medium are continually monitored. Even small changes or fluctuations of the concentration can have an influence on the product in sensitive processes.

Consequently, the task presents itself to develop a method and a measuring system for monitoring the ability of an amperometric electrochemical sensor to function properly, and to design the method and the measuring system in such a way that the method can be performed quickly, that it is independent of the composition of the medium and that it can also be used in processes with a variable composition of the medium.

SUMMARY OF THE INVENTION

The solution to this task is found in a method and in a measuring system according to appended claims.

A method of checking whether an amperometric electrochemical sensor with an electrochemical cell is functioning correctly comprises the following steps: A perturbation quantity is applied to the electrochemical cell after the latter has been operated under voltage control with an initially constant polarization voltage. The response, i.e. the measurement signal or the measurement value produced by the electrochemical cell as a result of the perturbation is registered, and the response to the perturbation of the electrochemical cell is used as an input in determining a check value. This check value is compared to a system-dependent or system-specific limit value, and the polarization voltage is either confirmed or changed. If the check value is smaller than or equal to the system-dependent limit value, the initial polarization voltage already represents the optimal polarization voltage. If on the other hand the check value is larger than the system-dependent limit value, the initial polarization voltage is changed by a predefined voltage increment. These steps are repeated with the changed polarization voltage until an optimal polarization voltage has been found, i.e. until the determination leads to a check value that is smaller than the system-dependent limit value.

Amperometric electrochemical sensors are operated in general with voltage control. It therefore suggests itself to use a voltage pulse as a perturbation quantity, so that the measuring system will not need to be switched between different operating modes. The measuring system itself will require only minor modifications to make it compatible with the method.

The voltage pulse used in performing the method can have different shapes and lengths. One could use, e.g., a rectangular pulse, a triangle-shaped pulse, a sinusoidal pulse, or a Gaussian pulse. The term "Gaussian pulse" in the present context means a pulse in the shape of a Gaussian bell curve. The pulse length can be adapted to the conditions in which the sensor is used and lies generally between one and sixty seconds. The amplitude of the perturbation pulse is between about one and about a hundred millivolt. It is advantageous to use small amplitudes, as the sensor can recover from small perturbations more quickly than from larger ones, meaning that after a perturbation the sensor will deliver constant measurement values again sooner after a perturbation of small amplitude.

The measurement value captured by an amperometric electrochemical sensor or the sensor response being measured is a current whose magnitude is in proportion to the partial pressure and/or the concentration of the substance dissolved in the medium.

If the actual polarization voltage is not equal to the optimal polarization voltage, the chemical system is influenced by the perturbation pulse and can be brought out of equilibrium. It has been shown that it is possible to establish a check function that represents a linear or non-linear relationship between the response of the system in the presence of a perturbation and the response in the absence of a perturbation. In the simplest case, the response of the system is the current being measured for a given polarization voltage at a given oxygen concentration. It is also conceivable that a time-dependent relationship is taken into account, for example between the perturbation pulse and the system response, or the amount of time it takes for the system to return to equilibrium. Based on the check function, it is possible to calculate a check value for a given perturbation pulse. The check function depends at least on the type of sensor being used, the medium under investigation, and the concentration that the substance to be investigated has in the medium.

The calculated check value is compared to a limit value which represents a measure for the sensor's ability to function correctly and for its measuring accuracy. The limit value is likewise system-dependent and is determined in such a way that the measuring accuracy of the sensor is within given tolerance limits as long as the limit value is complied with.

Accordingly, the limit value depends on a variety of factors which include the temperature, the type of sensor being used, its sensor geometry, as well as the concentration or the partial pressure that the substance under investigation has in the medium.

The check function as well as the limit value have to be determined individually for each sensor type, preferably through an empirical procedure. After the check function has been determined for a certain sensor type, the function can be stored for example in a database and/or in a processing unit which can be accessed by the method.

The method for checking the function of an amperometric electrochemical sensor is repeated in predetermined time intervals in order to determine whether and to what extent the system has moved away from its optimal setting. The time intervals for repeating the method are between a few minutes and several hours or days, preferably between about 5 minutes and 24 hours. Ideally, the method is carried out at least once per day of measuring.

If it is found in a function check that the actual polarization voltage deviates from the optimal polarization voltage, the actual polarization voltage is changed in steps and subjected anew to the function-check method after each adjustment. The change of the polarization voltage takes place in predetermined voltage increments which are prescribed to the user as given quantities dependent on the sensor and the medium. The voltage increments have a magnitude between 5 and 1000 mV and preferably between 10 and 150 mV.

The sensor response in terms of current depends on the temperature, and consequently the method for checking the function of the sensor as well as the determination of measurement values are preferably performed with temperature compensation. The temperature compensation is normally made on the basis of the actual temperature of the medium by normalizing the measurement value or the current response for a standard temperature. This is necessary because the solubility of a substance depends on the temperature and the latter also has an influence on the concentration of the substance in the solution.

The temperature of the medium is determined preferably by means of at least one suitable temperature sensor.

With a suitable measuring system, the function-checking method can also performed in an automated way, so that it can be integrated, e.g. in testing routines and/or process-monitoring routines.

A measuring system to carry out the method of the foregoing description includes at least one amperometric electrochemical sensor with at least one working electrode and a counter-electrode, a variable voltage source to generate a polarization voltage and the at least one perturbation pulse, a current-measuring device to determine the measurement values, and a computer-assisted control- and processing unit.

The function-checking method is implemented by way of an appropriate program in the computer-assisted control- and processing unit. The method as well as normal measurements can be carried out by means of the control- and processing unit.

The computer-assisted control- and processing unit further includes a data memory in which the system-dependent parameters for different substances, concentrations and sensor types are stored. These parameters include at least the values for the predetermined increments, the system-dependent limit values, the perturbation pulses and the initial polarization voltage as well as system-dependent check functions and the pertinent temperature data which are needed together with the parameters for the compensation of the measurement values.

The processing unit further includes a monitor and/or a loudspeaker so that an optical, electrical and/or acoustical signal can be generated when the conditions for breaking off have been met. This signal indicates to the user that a further manual check of the system should be performed which, in turn, can allow conclusions about changes in the medium.

Besides a working electrode and a counter-electrode, an electrochemical cell can also include a reference electrode.

The amperometric electrochemical sensor can have a gas-permeable membrane that is preferably permeable for oxygen. A membrane of this kind increases the sensitivity of the sensor.

BRIEF DESCRIPTION OF THE DRAWINGS

The method for checking the correct functioning of an amperometric electrochemical sensor is explained through a flowchart diagram and a preferred embodiment, supported by the drawings, wherein:

FIG. 1 shows a schematic representation in the form of a flowchart of a method for checking the function of a sensor, with the circled numbers 1 to 4 referring to the continuation of the flowchart;

DETAILED DESCRIPTION OF A PREFERRED EMBODIMENT

Figure 2:
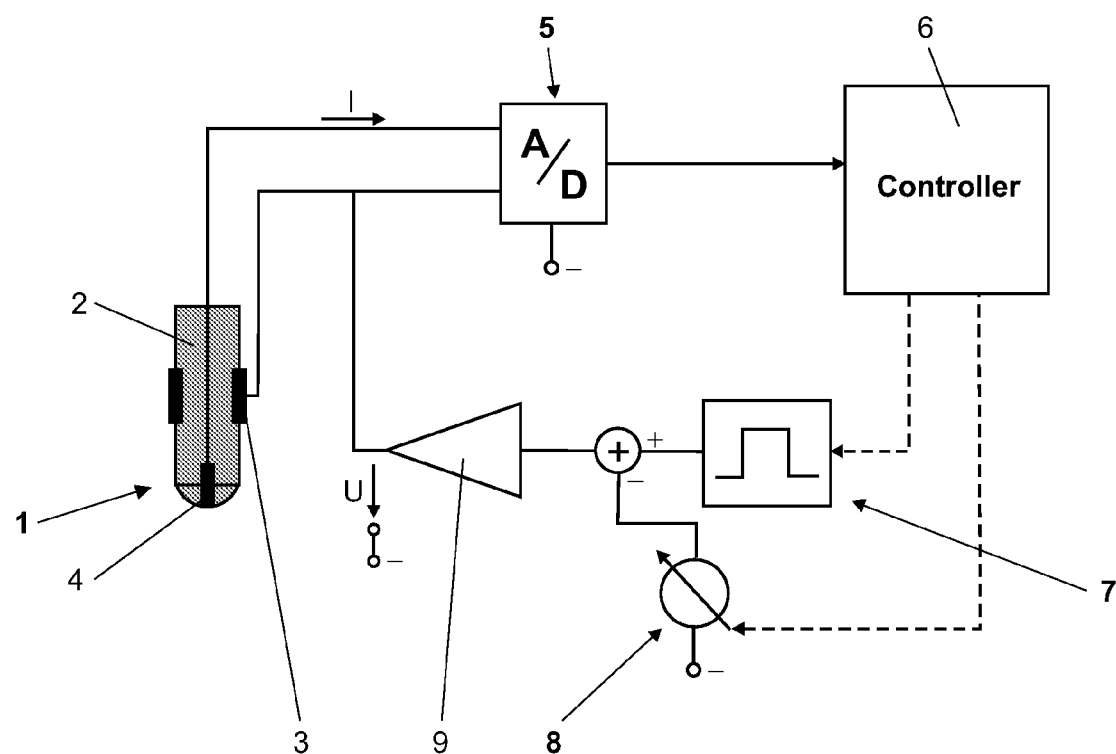
FIG. 2 represents a block schematic of a measuring system with an oxygen sensor.

The flow chart of FIG. 1 schematically illustrates the sequence of operations for the function check of an amperometric electrochemical sensor. An amperometric electrochemical sensor is operated with voltage control at a certain initial polarization voltage $U_s$. The quantity being measured is the initial current $I_s$ which corresponds to $U_s$ and is based on chemical reactions in the electrochemical cell of the sensor.

To check the ability of the sensor to function correctly, at least one perturbation pulse $\pm U_D$, preferably in the form of a perturbation voltage, is applied to the sensor. In general, the perturbation pulses $\pm U_D$ used are voltages of a magnitude from $\pm 10$ to about $\pm 50$ mV, wherein the perturbation pulse $\pm U_D$ can be positive or negative in relation to the initial polarization voltage $U_s$. The significance of this for the method is that the sensor can be subjected to either at least one individual positive or negative perturbation pulse, or first to at least one positive or negative perturbation pulse which is followed by at least one negative or positive perturbation pulse. The amplitude of $\pm U_D$ is selected depending on the sensor and the medium. The perturbation pulse $\pm U_D$ can have different pulse shapes such as a rectangular, triangular, or sinusoidal pulse shape, or it can be shaped like a Gaussian bell curve, with a rectangular-shaped pulse being preferred. The pulse length of the perturbation pulse $\pm U_D$ is preferably between about 5 and 60 seconds.

The medium in the electrochemical cell of the sensor reacts to the perturbation $\pm U_D$, and a current $I_D$ can be measured which corresponds to the perturbation $\pm U_D$.

A mathematical relationship, which in the ideal case is expressed by a linear check function K, exists between the sensor response $I_D$ of the system in the presence of a perturbation and the sensor response $I_S$ when there is no perturbation. However, the two quantities $I_D$ and $I_S$ can also be tied together through a non-linear function K. For an individual response $I_S$ and an individual response $I_D$ a check value $K_D$ is calculated from the mathematical relationship $K_D=|K(I_D,I_S)|$.

The check function K can include different mathematical connections between the response of the system without a perturbation and the response with a perturbation, such as a quotient, a difference, a sum, or a product of the responses, or also a linear, non-linear, polynomial, or exponential relationship. K can also be made equal to the response of the system with a perturbation. The check function can further include the time-dependent relationship between the perturbation pulse $\pm U_D$ and the response current. The check value $K_D$ is the absolute amount of the value of the check function K that was determined for a specific sensor and a specific substance concentration for a response of the sensor in the presence of a perturbation and a response without perturbation. The check value $K_D$ can also be calculated by means of the check function K based on an individual response pair or also based on a mean value of a plurality of measurement values and/or based on the time-dependent relationship between the values.

In a further step, this check value $K_D$ is compared to a system-dependent limit value $K_L$. The latter represents a measure for how far the polarization voltage of the sensor can deviate from an optimal polarization voltage with the sensor still functioning within its measurement uncertainty, i.e., without causing a significant measurement error. $K_L$ depends on the geometry of the sensor being used, on the temperature, as well as on the concentration or the partial pressure that the substance under investigation has in the medium. In the case of a computer-supported evaluation, it suggests itself to store the limit value $K_L$ for different sensor types, substance concentrations and temperatures in a database which can be accessed by an evaluation program and/or a processing unit. With preference, $K_L$ is determined empirically, and the determination procedure may offer the option of allowing user-specified accuracy requirements to be incorporated.

If the check value $K_D$ of the system with a perturbation is smaller than or equal to the limit value $K_L$, the sensor is working correctly within the given limits, and the set polarization voltage $U_S$ equals the optimal polarization voltage $U_{opt}$. This means for the electrochemical cell that the partial pressure at the cathode equals zero.

To check the function of the sensor on an ongoing basis, the method is repeated at predetermined time intervals as indicated by the connection between $U_S:=U_{opt}$ and $U_S$. The symbol ":=" indicates a definition, in this case, that $U_S$ is defined to be $U_{opt}$. The continual checking at predetermined time intervals serves to monitor the system over an extended time period and to keep checking and, if necessary, adjusting the polarization voltage on a regular basis.

However, if the check value $K_D$ of the system in the presence of a perturbation is larger than the limit value $K_L$, this indicates that the polarization voltage $U_S$ needs to be adjusted. A new polarization voltage $U_{-1}:=U_S-\Delta U$ is set on the sensor, corresponding to the initial polarization voltage $U_S$ reduced by a predefined voltage increment $\Delta U$. The magnitude of the voltage increment $\Delta U$ to be selected depends on the sensor being used and on the concentration of the substance in the medium. The values for $\Delta U$ can lie between about 5 and 1000 millivolt, with values between 10 and 150 millivolt being preferred.

A new polarization voltage $U_{-1}$ is set on the sensor, which produces a new sensor response current $I_{-1}$. After the sensor has been adjusted in this way, it is subjected again to at least one perturbation voltage pulse $\pm U_D$, and the response signal $I_{-1D}$ that the sensor delivers under the perturbation is measured. Based on the response $I_{-1}$ and the response $I_{-1D}$, a new check value $K_{-1}=|K(I_{-1D},I_{-1})|$ is calculated.

This check value $K_{-1}$ is again compared to the limit value $K_L$. If $K_{-1}$ is smaller than or equal to the limit value $K_L$, the initial polarization voltage $U_S$ has been changed in the direction of the optimal polarization voltage $U_{opt}$, and $U_{-1}$ corresponds to the optimal polarization voltage $U_{opt}$. The optimal polarization voltage $U_{opt}$ is set on the sensor and used for taking subsequent measurements. In other words, $U_{opt}$ becomes $U_S$. The method is subsequently repeated in predetermined time intervals in order to check and adapt the system continually.

On the other hand, if $K_{-1}$ is still larger than the limit value $K_L$, a comparison of $K_{-1}$ with $K_D$ follows as a further step.

If $K_{-1}$ is smaller than $K_D$, the initial polarization voltage $U_S$ was corrected in the right direction, but the correction was not strong enough. Neither the initial polarization voltage $U_S$ nor the first corrected polarization voltage $U_{-1}$ correspond to the optimal polarization voltage $U_{opt}$. The polarization voltage $U_{-1}$ therefore has to be lowered by a further voltage increment $\Delta U$, and the result is a new polarization voltage $U_{-2}:=U_{-1}-\Delta U$.

The new polarization voltage $U_{-2}$ is set, and the current $I_{-2}$ is measured. This is followed by subjecting the sensor again to at least one perturbation pulse $\pm U_D$, measuring the sensor response $I_{-2D}$, determining a new check value $K_{-2}$ and comparing the latter to the limit value $K_L$. If $K_{-2}$ is still larger than $K_L$, the polarization voltage is lowered by a further voltage increment so that $U_{-n}:=U_{-(n-1)}-\Delta U$, wherein n:=n+1 and $n\geq 2$ is an integer.

The new polarization voltage $U_{-n}$ is set, the response current $I_{-n}$ is measured, a perturbation is again applied to the sensor, the response $I_{-nD}$ of the system in the presence of the perturbation is measured, the check value $K_{-n}$ is determined and compared to the limit value $K_L$. This process is iterated until the latter comparison shows that $K_{-n}\leq K_L$, at which point the function check can be terminated by setting the polarization voltage.

If on the other hand $K_{-1}$ is larger than $K_L$ and larger than $K_D$, this indicates that the initial polarization voltage $U_S$ was corrected in the wrong direction. In this case, the test continues by setting a new polarization voltage $U_1:=U_S+\Delta U$ which corresponds to the initial polarization voltage $U_S$ with the addition of a voltage increment $\Delta U$, and the associated current strength $I_1$ is measured. This is followed by subjecting the sensor again to a perturbation pulse $\pm U_D$, measuring the sensor response $I_{1D}$, determining a check value $K_1$ as a function of $I_{1D}$ and $I_S$ and comparing the check value $K_1$ to the system-specific limit value $K_L$. If $K_1$ is smaller than or equal to $K_L$, the new polarization voltage $U_1$ corresponds to the optimal polarization voltage and is set and used for the subsequent measurements.

However, if $K_1$ is larger than $K_L$, the polarization voltage $U_1$ is increased again by a voltage increment $\Delta U$ so that $U_n:=U_{(n-1)}+\Delta U$, wherein n:=n+1, and $n\geq 1$ is an integer. The response $I_n$ of the system with the new polarization voltage $U_n$ is determined, the sensor is subjected to a perturbation pulse $\pm U_D$, the current strength $I_{nD}$ is measured, and a check value $K_n$ which is dependent on $I_{nD}$ and $I_n$ is calculated and compared to the limit value $K_L$.

The steps of setting a new polarization voltage $U_n$ or $U_{-n}$, determining the response current $I_n$ or $I_{-n}$, applying a perturbation pulse $\pm U_D$, measuring the response $I_{nD}$ or $I_{-nD}$ of the system in the presence of the perturbation, determining a check value $K_n = |K(I_{nD}, I_n)|$ or $K_{-n} = |K(I_{-nD}, I_{-n})|$ and comparing the check value $K_n$ or $K_{-n}$ to the system-specific limit value $K_L$ are now repeated until the check value $K_n$ or $K_{-n}$ is smaller than or equal to the limit value $K_L$. However, these steps are not repeated endlessly, but only as long as the polarization voltage $U_n$, $U_{-n}$ remains within a given voltage range, i.e. between $U_{max}$ and $U_{min}$. The two values $U_{max}$ and $U_{min}$ are sensor-specific values which indicate the voltage range in which a given sensor can or should in principle be operated. If the actual polarization voltage $U_n$ or $U_{-n}$ lies outside the given voltage range, the process is terminated and the user is informed by way of an acoustical, electrical and/or optical signal.

If the steps have been repeated until the condition $U_n \geq U_{max}$ or $U_{-n} \leq U_{min}$ for terminating the process has been met and an optimal polarization voltage $U_{opt}$ has not been found, this leads to the conclusion that at least a part of the measuring system needs to be checked or serviced. Strong deviations can be a sign that, e.g., the sensor or the membrane needs to be exchanged or the sensor needs to be filled with new electrolyte solution. Changes in the medium such as sudden pH changes or a change in composition are likewise possible but as a rule they occur rather seldom.

The fact that the condition for terminating the process has been reached is indicated to the user by means of an acoustical, electrical and/or optical signal of a computer-supported processing unit. It is also conceivable that the signal is sent electrically or electronically directly to a process control unit as a malfunction signal and that the process is either adapted or stopped.

The process illustrated in FIG. 1 can also be used for a continual automated function check of any kind of amperometric electrochemical sensor, for example during a chemical process.

This is done by repeating at predetermined intervals the method of the foregoing description for the polarization voltage that has been set. These time intervals lie between about 5 minutes and 24 hours, with about 30 minutes being the preferred time interval. Ideally, the function check is carried out at a time between two measurements, so that no gaps are caused in the measurement series. It would also be possible to correlate the frequency of taking measurements to the deviation of the optimal polarization voltage from the initial polarization voltage. If for example the deviation between $U_S$ and $U_{opt}$ is relatively large, measurements should be taken more frequently in order to better control the process.

In practical situations, the functionality of an amperometric electrochemical sensor should be checked very rigorously before the beginning or start of a process, especially since a good calibration can be performed only at the optimal polarization voltage. A repeated check at fixed time intervals can also be used to confirm the last-determined optimal polarization voltage by checking the system at regular time intervals. Furthermore, repeating the check several times in close succession allows a mean value to be determined for the optimal polarization voltage based on a sequence of several perturbation cycles, so that the determination of the optimal polarization voltage will be less affected by short-term fluctuations of the measuring system and/or by the composition of the medium.

Of course, it is also possible to apply more than one perturbation pulse $\pm U_D$ to the sensor, for example a certain number of negative and/or positive perturbation pulses followed by a certain number of positive and/or negative perturbation pulses, or to alternatingly apply positive and negative perturbation pulses to the sensor, and to form a mean value based on the calculated check values K.

The method is very flexible, as the parameters $U_D$, $\pm\Delta U$, K, $K_L$, as well as $U_{min}$ and $U_{max}$ can be individually adapted depending on the area of application and on the sensor type being used. Consequently, the method can be used for the functionality check of a multitude of amperometric electrochemical sensors.

$K_L$ is determined as a function of the substance concentration in the medium and of the temperature, and the method is therefore substantially independent of the composition of the medium and of the concentration of the substance dissolved in the medium, so that it can also be used for the functionality checking of sensors that are used to monitor media which may for example change over the course of a process. A change of the medium occurs for example in the course of reactions in which the substance under test is produced and/or consumed.

The polarization voltage $U_S$ is first reduced by $\Delta U$ to $U_{-1}$, but of course it is also possible to first increase the initial polarization voltage $U_S$ to $U_1$ by a predefined voltage increment $\Delta U$ and to check in a later step whether the initial polarization voltage $U_S$ was changed in the right direction.

Particularly for process-monitoring applications, it suggests itself that the method and the associated limit values $K_L$ which depend on the concentration of the test substance in the medium be integrated in a data-evaluating program which cooperates with the processing unit, so that the function check can be performed automatically and also on-line and the polarization voltage can be checked and, if necessary, adapted in predetermined time intervals.

FIG. 2 shows a system block diagram of a measuring system that serves to perform the method with an oxygen sensor. The oxygen sensor 1 is represented only schematically in this case. Immersed in an electrolyte solution 2 are a cathode 4 and an anode 3, the latter shown here in a ring-shaped configuration, to which a voltage U is applied. The current loop of the sensor is closed by way of an appropriate measurement circuit, in this case for example by way of an A/D converter 5 for the current I. The result of the measurement is delivered to the control- and processing unit 6.

The control- and processing unit 6 in which the method of FIG. 1 is implemented, evaluates the response current $I_{-1D}$, $I_{-2D}$, $I_{1D}$, $I_{-n}$, $I_n$ of the sensor and controls a perturbation pulse generator 7 as well as a variably settable voltage source 8 which by way of the amplifier 9 serves to set the optimal polarization voltage $U_{opt}$, the initial polarization voltage $U_S$ and/or the adjusted polarization voltage $U_{-1}$, $U_{-2}$, $U_1$, $U_{-n}$, $U_n$. The perturbation pulse generator 7 can produce perturbation pulses of different amplitudes, repetition rates and durations. With preference, the perturbation pulse has the rectangular shape shown in FIG. 2, but it is also possible to produce other pulse shapes. After amplification, the result is a superposition of the perturbation pulse $\pm\Delta U$ on the polarization voltage $U_S$, $U_{-1}$, $U_{-2}$, $U_1$, $U_{-n}$, $U_n$.

Figure 3:
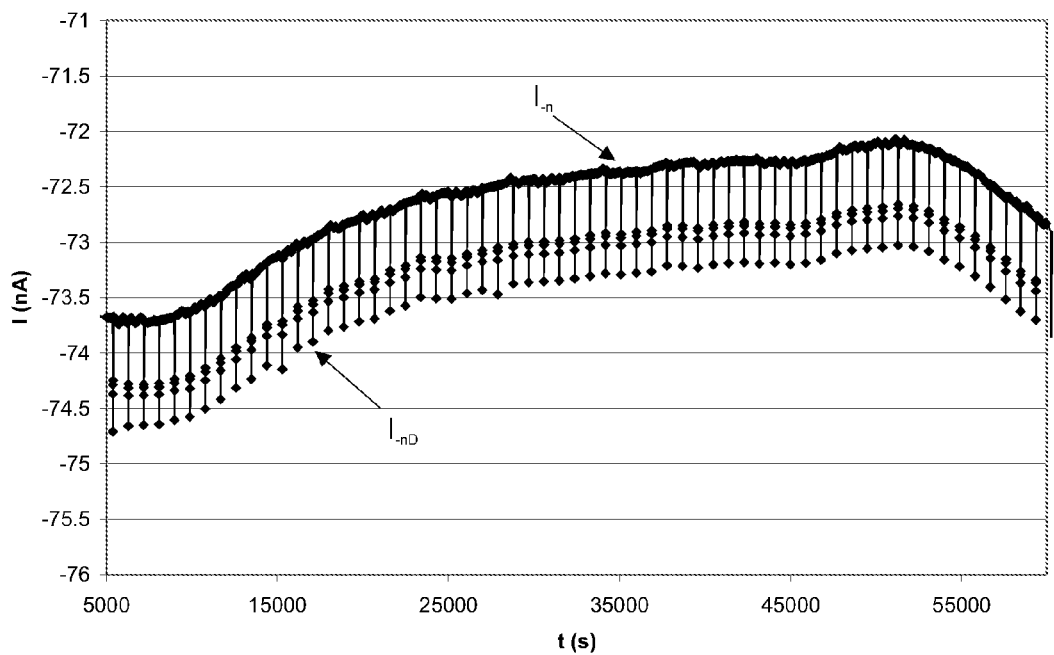
FIG. 3 represents a time profile of the current for an oxygen sensor InPro6800 operated in air.
Figure 4:
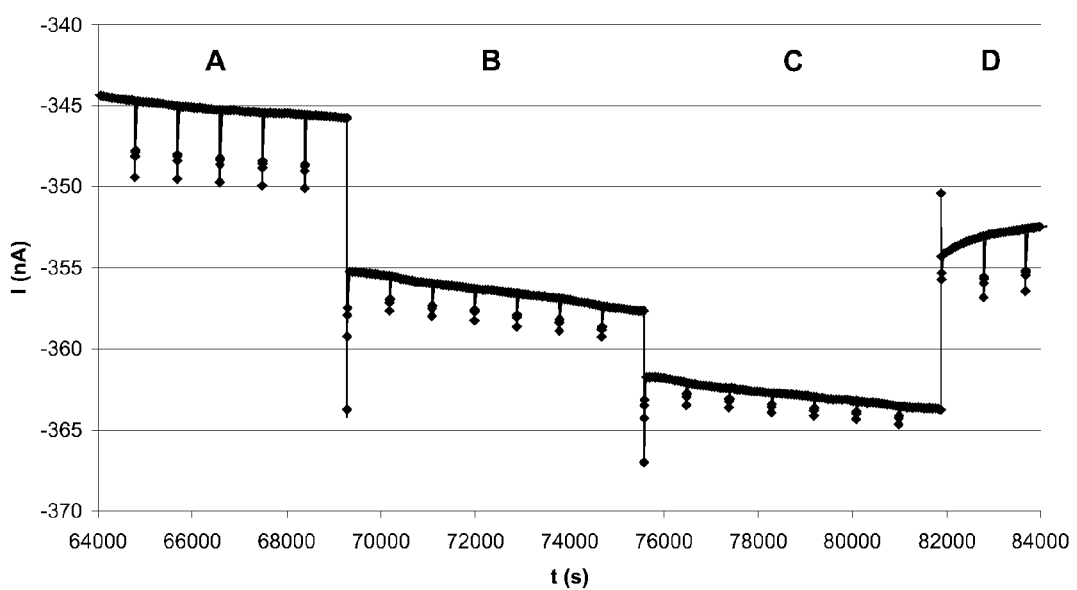
FIG. 4 represent a time profile of the current for an oxygen sensor InPro6800 operated in pure oxygen.

The following practical example shows with the help of FIGS. 3 and 4 how the method can be applied to an amperometric electrochemical oxygen sensor of the type InPro6800 (Mettler-Toledo) for media of different compositions.

The amperometric electrochemical oxygen sensor of the type InPro6800 includes a platinum cathode, a silver/silver-chloride anode and a state-of-the-art oxygen-sensitive membrane. The sensor is connected to a computer-supported processing unit and controlled by a program in which the method of FIG. 1 is implemented.

Sensors of the type InPro6800 are generally operated with an initial polarization voltage of −675 mV, while the range for the polarization voltage at which these sensors can be operated in principle is between −450 and −900 mV. To demonstrate the functionality-checking method according to FIG. 1, the sensor in this practical example is operated with an initial polarization voltage of only $U_S=-650$ mV. Atmospheric air with 21% oxygen is used as a measuring medium.

The diagram of FIG. 3 represents the current I, i.e., the sensor signal, at a polarization voltage of −650 mV as a function of the time t, the test medium being air. The sensor signal was determined every three seconds over a time period of 1000 minutes (60,000 seconds). Within this time frame, the function-checking method was performed in accordance with a predetermined time pattern. The polarization voltage was left at −650 mV for 120 seconds, at which point a perturbation pulse $\pm U_D$ with a duration of 12 seconds and an amplitude of −25 mV was applied to the system. A rectangular-shaped pulse was used as a perturbation pulse $\pm U_D$. The signals $I_{-nD}$ of the system in the presence of the perturbation can be seen in FIG. 3 as negative jumps or spikes occurring at regular time intervals, with a deviation of about −1 nanoampere in comparison to the signals $I_{-n}$ of the system without the perturbation. The time intervals of only 3 seconds between the measurement values are very short, so that for each perturbation pulse about four measurement values are taken.

The system reacts to this type of perturbation pulse with a likewise rectangular change in the current strength, although a chemical system is more sluggish than a purely electronic system. It reacts more slowly, so that the answer to the perturbation pulse in the form of a change in current occurs with some delay.

The sensor signal $I_{-n}$ of the system without perturbation shows a relatively constant current level with an absolute deviation of only about 1.6 nA, in a current range between about −73.7 and −72.1 nA. The fluctuations occur because the temperature sensor was operated without temperature compensation. Based on the signals $I_{-n}$ of the system without perturbation and $I_{-nD}$ with perturbation, a check value $K_{-n}$ is calculated in this practical example for each perturbation pulse, according to the following formula:

$$K_{-n} = \left| \frac{I_{-nD}}{I_{-n}} \cdot 100 \right|, \text{ with } n \geq 1,$$

wherein $I_{-n}$ is the response of the system without perturbation and $I_{-nD}$ is the response in the presence of the perturbation. The check value $K_{-n}$ is then compared to the system-specific limit value $K_L$ which is about 1% for this type of sensor in air. In spite of the fact that the initial polarization voltage was lowered, the check value calculated from the foregoing formula for all of the perturbation pulses lies still below the limit value $K_L$. This indicates that under the prevailing conditions the sensor still operates within the measurement accuracy specified for this sensor type.

FIG. 4 shows a continuation of the diagram of FIG. 3 along the time axis, but reflecting an abrupt change in the test medium from air to pure oxygen. The four time segments A, B, C, D represent time segments with different polarization voltages. To give a clear picture of the situation, each of the polarization voltage settings is held unchanged over a time period of 5000 seconds. During this time period, the polarization voltage was disturbed every 120 seconds by a rectangular perturbation pulse with a duration of 12 seconds and an amplitude of −25 mV, while a measurement value was acquired every three seconds.

The change of the medium while the sensor and the polarization voltage stay the same has an immediate effect on the sensor signal. With an initial polarization voltage of −650 mV, the sensor produces a sensor signal in pure oxygen which in comparison to the signal in air (see FIG. 3) has changed from about −73 nA to about −345 nA (see time segment A). If the system is disturbed by perturbation pulses, the system will react to the perturbation pulses with some delay and will show pulses that are likewise negative, as can be seen in FIG. 4.

Based on at least one measurement signal with the initial polarization voltage of −650 mV (see time segment A) and at least one response of the disturbed system, the check value $K_{-n}$ is calculated in each case, whose mean value of 0.9% is clearly higher than the limit value $K_L$ for pure oxygen. The value of $K_L$ for pure oxygen should be equal to or below 0.3%.

Analogous to the method shown in FIG. 1, the polarization voltage is lowered in voltage increments of $\Delta U=-100$ MV, the system is subjected to a perturbation, a new check value $K_{-n}$ is calculated based on the response currents of the non-disturbed and the disturbed system, and the new check value $K_{-n}$ is compared to the system-specific limit value $K_L$.

In this practical example the lowering of the polarization voltage coincides with sending a perturbation pulse, so that the signal of the system changes more strongly than would be the case if the perturbation were applied to the system while maintaining the same polarization voltage. The abrupt change of the polarization voltage also has an influence on the electrode reactions, so that it takes some time until equilibrium has established itself again.

The time segment B illustrates the measurement signals of the system in the disturbed and non-disturbed state with a polarization voltage of −750 mV. Based on the values of the measurement signals between the signals of the system in the disturbed and non-disturbed state and based on the relationship which was already stated above for air as a medium, the check value was determined to be 0.3%.

In the time segment C the polarization voltage is lowered again by $\Delta U=-100$ mV to a level of −850 mV, whereby the check value is lowered further to 0.2%.

For pure oxygen, the limit value for this type of sensor should be at about 0.3%. In relation to the results illustrated in FIG. 4, this means that with a polarization voltage of −750 mV as well as with a polarization voltage of 850 mV the sensor is operating optimally within the given limits, with a lower check value being preferred because the measurement error will also be lower.

Next, as a check of the method, the polarization voltage is raised again manually to −650 mV (see time segment D). In response, the current increases again and the calculated check values of 0.7% are also clearly above the limit value.

The example presented here shows the use of the method delineated schematically in FIG. 1 for a function check of an amperometric electrochemical sensor.

The example relates to a specific type of oxygen sensor. However, the method can also be used analogously for other amperometric electrochemical sensors, in which case the limit value $K_L$ and other method parameters have to be adapted to the measuring system and to the medium being measured by the sensor.

The method for checking the function and adjusting the polarization voltage can also be used for measurements in media that contain substances which interfere with the measurement. An example of such an interfering substance is carbon dioxide. Dissolved carbon dioxide lowers the pH value of the electrolyte solution, so that hydrogen can be released in the reduction already at lower polarization voltages, which will falsify the measuring result.

What is claimed is:

1. A method of checking the function of an amperometric electrochemical sensor which comprises an electrochemical cell, comprising the steps of:
   a. applying a constant polarization voltage to the electrochemical cell, the first application of the constant polarization voltage being a constant initial polarization voltage;
   b. applying a perturbation quantity to the electrochemical cell;
   c. determining at least one response of the electrochemical cell in the presence of the perturbation;
   d. determining a check value by using the at least one electrochemical cell response;
   e. comparing the check value to a limit value to determine a variance such that when the variance is positive, the constant polarization voltage is changed by a predetermined increment and steps a. through e. are repeated with the changed polarization voltage; and when the variance is zero or negative, the polarization voltage is determined to be an optimal polarization voltage.

2. The method of claim 1, wherein the sensor is operated with voltage control and temperature compensation during the function check.

3. The method of claim 2, wherein the check value determining step uses a check function which is system-specific and establishes a mathematical relationship between the electrochemical cell response in the presence of the perturbation and the electrochemical cell response without the perturbation.

4. The method of claim 3, wherein the check function is determined empirically prior to applying the perturbation quantity and is stored in a processing unit.

5. The method of claim 4, wherein the perturbation quantity is a voltage pulse selected from the group consisting of: rectangular, triangular, sinusoidal and Gaussian.

6. The method of claim 5, wherein the voltage pulse is effective in the system for a duration of 1 to 60 seconds with a maximum value of 100 mV.

7. The method of claim 6, wherein the voltage increment is between 5 and 1000 mV.

8. The method of claim 7, wherein the voltage increment is between 10 and 150 mV.

9. The method of claim 7, wherein the method is performed automatically.

10. The method of claim 1, wherein the check value determining step uses a check function which is system-specific and establishes a mathematical relationship between the electrochemical cell response in the presence of the perturbation and the electrochemical cell response without the perturbation.

11. The method of claim 10, wherein the check function is determined empirically prior to applying the perturbation quantity and is stored in a processing unit.

12. The method of claim 1, wherein the perturbation quantity is a voltage pulse selected from the group consisting of: rectangular, triangular, sinusoidal and Gaussian.

13. The method of claim 12, wherein the voltage pulse is effective in the system for a duration of 1 to 60 seconds with a maximum value of 100 mV.

14. The method of claim 1, wherein the voltage increment is between 5 and 1000 mV.

15. The method of claim 14, wherein the voltage increment is between 10 and 150 mV.

16. The method of claim 1, wherein the method is performed automatically.

17. A measuring system for performing the method of claim 1, comprising:
   an amperometric electrochemical sensor which has an electrochemical cell with at least one working electrode and a counter-electrode, a variably settable voltage source, a current-measuring device, and a computer-supported control- and processing unit in which the method according to claim 1 is implemented.

18. The measuring system of claim 17, wherein the computer-supported processing unit comprises a data memory in which the values for the predetermined increments, the limit values, the perturbation pulses and the initial polarization voltage as well as the check function are stored for different substance concentrations and different sensors.

* * * * *

UNITED STATES PATENT AND TRADEMARK OFFICE
CERTIFICATE OF CORRECTION

PATENT NO. : 7,691,254 B2  Page 1 of 1
APPLICATION NO. : 11/276988
DATED : April 6, 2010
INVENTOR(S) : Oberlin It is certified that error appears in the above-identified patent and that said Letters Patent is hereby corrected as shown below:

In column 8, line 41, please delete "$n \geqq 2$" and insert -- $n \geq 2$ --.

In column 8, line 47, please delete "$K_{-n} \leqq K_L$" and insert -- $K_{-n} \leq K_L$ --.

In column 8, line 66, please delete "$n \geqq 1$" and insert -- $n \geq 1$ --.

In column 9, line 23, please delete "$U_n \geqq U_{max}$ or $U_{-n} \leqq U_{min}$" and insert -- $U_n \geq U_{max}$ or $U_{-n} \leq U_{min}$ --.

Signed and Sealed this

Fifteenth Day of June, 2010

David J. Kappos
*Director of the United States Patent and Trademark Office*